(12) United States Patent
Floren et al.

(10) Patent No.: US 10,352,924 B2
(45) Date of Patent: Jul. 16, 2019

(54) NANOFIBROUS PHOTOCLICKABLE HYDROGEL MICROARRAYS

(71) Applicant: The Regents of the University of Colorado, Denver, CO (US)

(72) Inventors: Michael Floren, Boulder, CO (US); Wei Tan, Broomfield, CO (US); Sadhana Sharma, Boulder, CO (US); Stephanie Bryant, Boulder, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 345 days.

(21) Appl. No.: 14/991,889

(22) Filed: Jan. 8, 2016

(65) Prior Publication Data

US 2016/0202241 A1 Jul. 14, 2016

Related U.S. Application Data

(60) Provisional application No. 62/101,334, filed on Jan. 8, 2015.

(51) Int. Cl.
*C12Q 1/02* (2006.01)
*G01N 33/50* (2006.01)
*C12N 11/04* (2006.01)
*B01L 3/00* (2006.01)
*C40B 60/12* (2006.01)

(52) U.S. Cl.
CPC .......... *G01N 33/502* (2013.01); *B01L 3/5085* (2013.01); *C12N 11/04* (2013.01); *G01N 33/5023* (2013.01); *G01N 33/5026* (2013.01); *B01J 2219/00385* (2013.01); *B01J 2219/00644* (2013.01); *B01J 2219/00743* (2013.01); *B01L 2300/069* (2013.01); *B01L 2300/089* (2013.01); *B01L 2300/123* (2013.01); *C40B 60/12* (2013.01)

(58) Field of Classification Search
CPC ..................................................... C12Q 1/025
See application file for complete search history.

(56) References Cited

U.S. PATENT DOCUMENTS 8,048,446 B2 * 11/2011 Lelkes ..................... A61L 27/26
424/422
2009/0221441 A1 * 9/2009 Lee ..................... G01N 33/5014
506/10

* cited by examiner

*Primary Examiner* — Rosanne Kosson
(74) *Attorney, Agent, or Firm* — Sheridan Ross P.C.

(57) ABSTRACT

Nanofibrous hydrogel microarray systems that act as facile, high throughput platforms for in vitro drug discovery and investigation and screening of combinatorial effects of physical and biochemical cues on maturation and differentiation of mammalian cells.

6 Claims, 3 Drawing Sheets

NANOFIBROUS PHOTOCLICKABLE HYDROGEL MICROARRAYS

CROSS REFERENCE TO RELATED APPLICATION

This application claims the benefit of priority under 35 U.S.C. § 119(e) to U.S. Provisional Patent Application Ser. No. 62/101,334, filed Jan. 8, 2015 which is incorporated herein in by reference.

GOVERNMENT INTEREST

This invention was made with Government support under grant numbers K25HL097246 and R01 HL119371 awarded by the National Institutes of Health (NIH). The U.S. Government has certain rights in this invention.

TECHNICAL FIELD

The invention relates to the production of hydrogel microarrays useful for high throughput screening of engineered microenvironments.

BACKGROUND

There is abundant evidence that local signals from tissue-specific extracellular matrix microenvironments significantly affect cellular differentiation, phenotypic expression and maintenance. Substrate biophysical signals, such as soluble factors, cell-ligand interactions, matrix elasticity and geometry play a critical role in a diversity of biological events including cell adhesion, growth, differentiation, and apoptosis. Together, these signals converge to provide a multifaceted, complex mechano-chemical signaling environment for highly-specific tissue morphogenesis and regeneration. Despite accumulated knowledge regarding individual and combined roles of various mechano-chemical ECM signals in stem cell activities, the intricacy exhibited by cellular microenvironments poses a considerable challenge in resolving the mechanisms ascribed to stem cell behavior and fate processes. This complexity mandates a systemic approach whereby integrative studies must be expanded to capture a more comprehensive understanding of the determinants which direct stem cell differentiation toward desired cell type and function. Conventional methods to elucidate these mechanisms have traditionally been executed in large scale, two-dimensional tissue culture platforms which are often limited by combinatorial brevity, substrate production, and reagent supply. Furthermore, these signals, matrix and biophysical microenvironment, are often observed independently to differentiate cells on 2D substrates, an environment vastly different from the way cells are presented naturally in vivo, i.e. in 3D tissue, which elicits multiple signal inputs to regulate cell fate.

High through-put approaches have emerged in recent years to circumvent the limitations of traditional low-through-put techniques (i.e. conventional cultureware), with the promise of developing complex platforms for combined biomolecule/substrate discovery. The salient features of microarray technology include the reproducibility and screening of multiple microenvironments with significantly less reagent and substrate requirements than traditional methods, while lending improved deconstruction of complex multivariable studies. Several reports have demonstrated ECM protein microarrays, soluble factor screening, biomaterial chemistry screening, and multiple signal integration arrays (i.e. elasticity and chemical factor) with encouraging results. However, despite the versatility afforded by current microarray technologies, the incorporation of multiple signals within engineered microarrays remain limited, and combinatorial microarray technologies in three-dimensions, coupled with other biophysical properties, such as tunable stiffness and geometry, have not been demonstrated. Capturing complex, multifaceted 3-dimensional environments in high-throughput with combinatorial signaling will likely prove a necessity in designing and using tissue regeneration biomaterial platforms.

SUMMARY

This disclosure provides a microarray platform based on electrospun nanofibrous hydrogels that can be used for screening of microenvironmental factors that influence cell maturation and differentiation in a high throughput manner. The nanofibrous hydrogels may be photoclickable thiol-ene poly(ethylene glycol) hydrogels, which polymerize by an orthogonal, step-growth mechanism wherein one thiol reacts with one ene' leading to a highly homogenous distribution in crosslinks. The nanofibrous hydrogels may also be poly (ethylene glycol) dimethacrylate polymers that undergo chain growth polymerization. The electrospun nanofibrous hydrogel microarray platforms of this disclosure provide good control over substrate elasticity and enable post-functionalization of the already prepared electrospun hydrogel substrates with extracellular matrix (ECM) molecules, such as peptides, with high reactivity and specificity.

This disclosure provides a thiol-ene poly(ethylene glycol) fiber cell culture substrate. The hydrogel fiber substrate may comprise a plurality of microspot or microdot islands that comprise one or more biomaterials. The biomaterials may include a polysaccharide, a proteoglycan, a glycosaminoglycan, a cell membrane bound protein, a growth factor, a peptide signaling motif, a hormone, or combinations of these materials. The hydrogel fiber substrate may be anchored to a solid support, such as a glass substrate. The hydrogel fiber substrate may be seeded with mammalian cells, such as stem cells.

This disclosure also provides methods of making a thiol-ene poly(ethylene glycol) fiber cell culture substrate. The method comprises forming a hydrogel fiber into a 3-dimensional nanofibrous matrix; and, anchoring the 3-dimensional nanofibrous matrix to a solid support to form a cell culture matrix. An array of biomaterial microdots may then be deposited onto the 3-dimensional nanofibrous matrix. Additionally or alternatively, a suspension of mammalian cells may be seeded onto the 3-dimensional nanofibrous matrix.

The culture substrates of this disclosure are useful for culturing one or more cell types that adhere to each location comprising an insoluble and/or soluble material (e.g., an adherence material).

This disclosure also provides methods of high throughput screening of engineered microenvironments by first forming an in vitro a thiol-ene poly(ethylene glycol) hydrogel fiber cell culture substrate anchored to a solid support, including biomaterial microdots arrayed on the hydrogel fiber and at least one mammalian cell seeded within the hydrogel fiber. An activity of the mammalian cell(s) is then monitored. The cellular activity may include gene expression, cell function, metabolic activity, cellular morphology, or combinations thereof. These methods may include contacting the mammalian cell(s) with a test agent prior to, or after, measuring a cellular activity. The test agent may include a growth factor, a hormone, a putative anti-cancer compound, a cell-surface protein inhibitor, a putative angiogenesis inhibitor, a modulator of Epithelial-Mesenchymal Transition (EMT), or combinations thereof.

Other aspects of this disclosure will be understood from the drawings, the detailed description, and examples provided below.

DESCRIPTION OF EMBODIMENTS

Figure 1A:
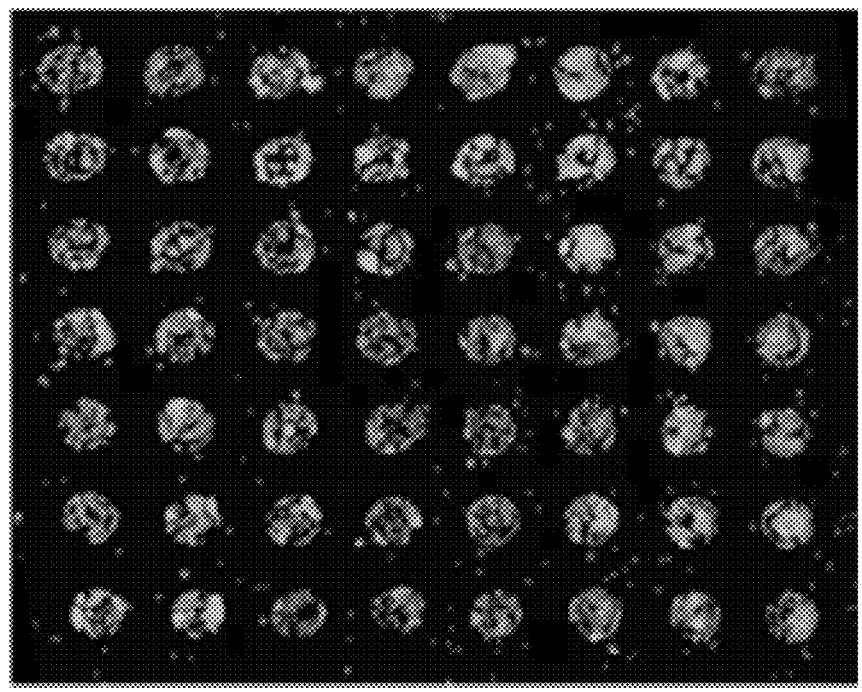
FIG. 1A shows rat mesenchymal stem cells (rMSCs) cultured for 24 hours on neo-tissue protein arrays. The image is a magnification of one printed subarray exhibiting discrete cellular "islands.

As used herein and in the appended claims, the singular forms "a," "and," and "the" include plural referents unless the context clearly dictates otherwise. Thus, for example, reference to "a spot" includes a plurality of such spots and reference to "the cell" includes reference to one or more cells, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application.

The need for engineered stem cell niches integrating several extrinsic stimuli has become a significant challenge within the research community. Due to the lack of current traditional methods to accurately and efficiently capture these complex microenvironments we adopted a high throughput method whereby matrix physical properties and biological ligands could be modulated. The design of a multivariate protein microarray for screening of SC microenvironments required the fabrication of an appropriate platform incorporating a three-dimensional substrate with nanofiber architecture and tunable elasticity and finally the integration of a combinatorial ECM protein microarray upon our engineered substrates.

The cellular microenvironment plays a critical role in determining cell fate and function. Extracellular determinants of survival, proliferation, migration, and differentiation include soluble signals (cytokines, dissolved gasses), insoluble cues (extracellular matrix, cell-cell interactions, biomaterials), and physical stimuli (shear stress). Miniaturization of bioassays using multiwell plates and robotic liquid handling enables combinatorial screening of the effects of soluble species on cellular behavior; however, analogous approaches for screening the effects of insoluble cues are in their infancy. Cellular interactions with the extracellular matrix (ECM) are of particular interest as ligation of an integrin can directly induce cellular signaling, modulate the response to other agonists, and influence the behavior of other integrins, a phenomenon called crosstalk. Thus, the extracellular matrix plays a role in developing an integrated picture of the microenvironment in the fate of many diverse cell types.

Cell-ECM interactions have been studied using several approaches. Typically, purified matrix proteins are adsorbed to cell culture substrates alone or in a combination requiring on the order of 10 .mu·g of protein per 96-well plate. These '2-dimensional' approaches are complemented by so-called '3-dimensional' approaches such as embedding cells within ECM gels. More complex ECM has also been investigated using cell-derived matrix in vitro or decellularized tissue sections. In addition to natural ECM components, biomaterial approaches have yielded several hybrid matrices with tethered biomolecules and tunable degradation in a 3-dimensional hydrogel context. Studies of the interaction of cell-ECM provides a critical first step towards developing a comprehensive understanding of insoluble cues in the cellular microenvironment.

Growth factor signals synergistically interact in permissive ECM microenvironments. Cross talk between ECM proteins and soluble growth factors would be best investigated using a highly parallel microfluidic platform integrating robotic spotting of substrates on a 3-dimensional cellular matrix, generating combinatorial soluble factor mixtures. Such a platform can be used in other experiments to investigate other cellular pathways involving multiple soluble factor interactions and integrin cross talk to study the combined effect of soluble and insoluble factors on cell fate and function.

This disclosure provides a robust method to create 3-dimensional cell matrices composed of hydrogel fibers that are spotted with protein or other biomaterials in an array using a spotter device (e.g., a DNA spotter device). The design of this microarray substrate was an important requisite of our studies of the effects of ECM, which necessitated a cellular matrix with tunable elasticity, three-dimensional architecture, reproducible fabrication, and ease of sample production. The cell culture matrices of this disclosure provide each of these advantages as well as other advantages described below.

Culturing mammalian cells, including especially stem cells, on combinatorial mixtures of extracellular matrix (ECM) proteins in the methods and cell matrices of this disclosure yields novel insights into the role of the microenvironment that may not be available using conventional 2-dimensional tissue culture methods. The methods and systems of this disclosure are amenable to depositing almost any insoluble or soluble material/biological material, such as polysaccharides, proteoglycans, glycosaminoglycans, membrane bound proteins, DNA, siRNA, and tethered growth factors or peptide signaling motifs. The methods and systems can also be easily adapted to: exploit lineage-specific fluorescent reporter strategies, co-cultivation of epithelia and stroma, and/or combinations of soluble factors to screen the effects of growth factors or small molecules in conjunction with underlying ECM structure and protein chemistry.

The cell culture matrix of this disclosure comprises a biologically compatible fiber anchored to a substrate or solid support. The fiber may be natural material (such as collagen, gelatin, elastin), or a synthetic polymer (such as PCL, PLGA, PLA, PS, PES), and/or synthetic and natural hydrogels (such as PEG-based hydrogels, silk protein). Hydrogels provide for hydration of bound cells, lack of diffusion of insoluble materials, low background binding of cells and free flow of cells across the surface of the microarray due to weak cell repulsion. The hydrogel fiber may be a poly (ethylene glycol) (PEG) polymer fiber. The hydrogel fiber may include a poly(ethylene glycol) dimethacrylate hydrogel, and/or a thiol-ene poly(ethylene glycol) hydrogel. Other examples of hydrogels useful in the methods and systems of this disclosure may include polyvinylalcohol (PVA), physically cross-linked by partial crystallization of the chain and/or hydrogels based on segmented polyurethanes or polyureas, polypeptide or polysaccharide hydrogels, such as agarose or cross-linked hyaluronic acid, partially hydrolyzed or aminolyzed polyacrylonitrile (PAN), so long as the hydrogel materials are sufficiently biocompatible and do not release harmful substances.

The hydrogel fiber may have an average fiber diameter between about 0.1 μm to about 3 μm. The hydrogel fiber may have an average fiber diameter between about 0.2 μm to about 0.6 μm in the dry state. The hydrogel fiber may have an average fiber diameter between about 0.4 μm to about 3 μm in the wet, or hydrated state. The hydrogel fiber may have an elastic modulus between about 0.4 kPa to about 15 kPa. The hydrogel fiber may have an elastic modulus between about 1 kPa to about 5 kPa.

The substrate used in the methods and systems of this disclosure can be made of any material suitable for culturing mammalian cells. For example, the substrate can be a material that can be easily sterilized, such as plastic or other artificial polymer material, so long as the material is biocompatible. The substrate can be any material that allows the hydrogel fibers to adhere (or can be modified to allow the hydrogel fibers to adhere, or not adhere at select locations). Various substrates or solid supports can be used to anchor the hydrogel fiber in the methods and systems of this disclosure. Such substrates include, but are not limited to, glass, plastics such as polystyrene and/or polypropylene, metals such as stainless steel, silicon and the like, including, but not limited to, polyamides; polyesters; polystyrene; polypropylene; polyacrylates; polyvinyl compounds (e.g. polyvinylchloride); polycarbonate (PVC); polytetrafluoroethylene (PTFE); nitrocellulose; cotton; polyglycolic acid (PGA); cellulose; dextran; gelatin, glass, fluoropolymers, fluorinated ethylene propylene, polyvinylidene, polydimethylsiloxane, polystyrene, and silicon substrates (such as fused silica, polysilicon, or single silicon crystals), and the like. Also metals, such as gold, silver, or titanium films, can be used.

The choice of the solid support should be taken in to account where biocompatibility with the cells or biomaterials or drugs that will be used in the cellular matrices may be effected. The solid support can be chosen from any number of rigid or elastic supports. For example, the solid support can comprise glass or polymer microscope slides.

At least one surface of the solid support may be treated or modified with a chemical, such as 3-(Trimethoxysilyl)propyl methacrylate (TMPMA), and/or a silicone compound such as 3-(mercaptopropyl) triethoxysilane. The solid support may also be modified with other chemicals, such as other acrylamide compounds, agarose, pluronics, serum albumin, or polyethylene glycol. The substrate may be densely hydroxylated prior to silanization, a highly porous glass substrate, or alternate silane coupling agents.

Alternatively, the hydrogel can be modified such that cell attachment is inhibited for a short period of time or in specific regions. During this period or in these regions, a spotter device may be used to deposit an etching solution (such as a mild periodic acid solution) to a hydrogel surface containing a degradable component. These regions can then be further modified by subsequently depositing protein solutions or pre-polymer solutions (with or without proteins) to the locations. Proteins or pre-polymer solutions can thus be immobilized on the solid support using photo-gelation or chemical crosslinking. Additionally, degradable polymer matrices can be incorporated into the hydrogel substrate that would allow for local sustained release of soluble factors. Each region may be tailored individually using these techniques.

The hydrogel fibers may be tuned or formed to retain specific biological molecules including, but not limited to, proteins, peptides, oligonucleotides, polynucleotides, polysaccharides, lipids and other biological molecules (i.e., "biomaterials"). A deformable hydrogel can be used in the methods and systems of this disclosure. Deformable hydrogels include polyacrylamide hydrogels. The hydrogel may include components that weakly repulse cells, thereby providing low background binding. The substrate and/or the hydrogel fibers may comprise a polymerized mixture including acrylamide and hydrophilic acrylates.

Hydrogels may be selected such that specific binding of desired biomaterials, including specific cell types is promoted and non-specific binding is reduced. Those of skill in the art will understand that cells vary in their ability to adhere to a cell culture matrix material and/or substrate material.

The hydrogel fibers acts as a deformable membrane that allows for seeded cells to be actively stretched during culture. Membrane deformation can be controlled using any of a multitude of suitable methods. These include MEMS motors incorporated into the cell culture matrix or on the solid support, and connected to the culture substrate and electroactive polymers that respond to electric field by undergoing a shape change. Examples of such materials include electrostrictive materials such as thin acrylate films with deformable electrodes placed on both sides of the material. An applied electric field causes the acrylate film to compress or expand, resulting in a concurrent change in surface area such that the total volume of the film remains constant. Such materials are known as "electrostrictive" in the field of electroactive polymers. Methods for generating force and deformation in a pliable material using electric fields ("electrophoretic"), or alternating non-uniform electric fields ("dielectrophoretic") are also possible by using a material that is responsive to such modes of excitation. As an example, the hydrogel fiber may incorporate charged particles, or neutral particles that can experience an induced dipole force in the presence of a uniform or non-uniform electric field. The electric field can be generated by placing the gel material on an electrode array, which can apply a static electric field, or an alternating electric field of the appropriate frequency to induce a net force on the dielectric medium of the gel.

By deformable is meant that a deformable material is capable of being damaged by contact with a rigid instrument. Examples of deformable materials include hydrogels, polyacrylamide, nylon, nitrocellulose, polypropylene, polyester films, such as polyethylene terephthalate, and the like. Non-deformable materials include materials that do not readily bend, and include glass, fused silica, nanowires, quartz, plastics (e.g. polytetrafluoroethylene, polypropylene, polystyrene, polycarbonate, and blends thereof) and the like; metals (e.g. gold, platinum, silver, and the like). A deformable material may be layered upon a non-deformable material.

The hydrogel fiber may be produced as a fiber on a solid substrate (e.g., a glass slide, cell culture plate, and the like), by mixing a solution of a monomer, a crosslinker, and a catalyst and/or an initiator and forming a fiber. The monomer and crosslinker may be prepared in one solution of an amount of initiator added. The solution is polymerized and crosslinked either by ultraviolet (UV) radiation or other appropriate UV conditions, or by thermal initiation at elevated temperature. The elasticity of the polymeric fiber matrix is controlled, or "tuned", by changing the amount of crosslinker and/or the percent solids in the monomer solution, and/or the exposure to UV/light. The polymerization may also be initiated by UV/light exposure.

The fiber may be formed by a fabrication technique such as electrospinning, electrospraying, spin-coating, and/or deposition by dipping.

Following fabrication, unpolymerized monomer is washed away, typically with water, leaving a nanofibrous gel matrix. Further lithographic techniques known in the semiconductor industry can be used to generate patterned structures in the nanofibrous matrix. Light may be applied to discrete locations on the matrix to further tune or activate specified regions, for example for the attachment of an oligonucleotide, an antibody, an antigen, a hormone, hormone receptor, a ligand or a polysaccharide on the matrix.

For hydrogel-based arrays using polyacrylamide, biomolecules can be prepared by forming an amide, ester or disulfide bond between the biomolecule and a derivatized polymer comprising the cognate chemical group. Covalent attachment of the biomolecule to the polymer is usually performed after polymerization and chemical cross-linking of the polymer is completed.

Controlled-release of soluble factors from a degradable polymer substrate has been demonstrated in the fields of drug delivery and biomimetic engineered surfaces. Typically, soluble factors are immobilized within a polymer matrix or hydrogel. As the matrix degrades, soluble factors are released into the environment. The degradation of the polymer, and thus the release kinetics, can be tailored by modifying the composition of the polymer or hydrogel. In one variation, growth factors are incorporated into poly(lactide-co-glycolide) (PLGA) microspheres. The GF-laden microspheres are then incorporated into a suitable matrix, such as PEG-hydrogel, PLGA, or acrylamide.

The nanofibrous matrix may be modified to promote cellular adhesion and growth. For example, the fiber may be treated with protein (i.e., a peptide of at least two amino acids) such as collagen or fibronectin to assist cells in adhering to the substrate. The proteinaceous material may be used to produce an array in or on the substrate. The array produced by the protein serves as a "template" for formation of a cellular microarray. A single protein may be adhered to the fiber, although two or more proteins may be used to spot the fiber using a device, such as a spotter device. Proteins that are suitable for use in modifying the fiber to facilitate cell adhesion include proteins to which specific cell types adhere under cell culture conditions, for example, collagen, fibronectin, gelatin, collagen type IV, laminin, entactin, and other basement proteins, including glycosaminoglycans such as heparin sulfate. Combinations of such proteins may also be used.

Depositing or patterning biomaterials on the nanofibrous matrix may be achieved using various micro-spotting techniques. Spotting techniques involve the precise placement of materials at specific sites or regions using automated techniques. Conventional physical spotting techniques such as quills, pins, or micropipettors are able to deposit material on the matrix in the range of 10 to 250 microns in diameter (e.g., about 100 spots/microwells per well of a 96 well culture plate). In some instances, the density can be from 400 to 10000 spots per square centimeter, allowing for clearance between spots. Lithographic techniques, such as those provided by Affymetrix (e.g., U.S. Pat. No. 5,744,305, the disclosure of which is incorporated by reference herein) can produce spots down to about 10 microns square, with no clearance between spots, resulting in approximately 800,000 spots per square centimeter. Insoluble and/or soluble materials may be spotted in very small, e.g. nanoliter, increments using a spotting device. The spotting device may employ one or more piezoelectric pumps, acoustic dispersion, liquid printers, micropiezo dispensers, or the like to deliver such reagents/biomaterials. The spotting device may comprise an apparatus and method like or similar to that described in U.S. Pat. Nos. 6,296,702, 6,440,217, 6,579,367, and 6,849,127. An automated spotting device may be used (e.g. Perkin Elmer BIOCHIP ARRAYER™. A number of contact and non-contact microarray printers are available and may be used to dispense/print the soluble and/or insoluble biomaterials on the nanofibrous matrix. For example, BIOCHIP ARRAYER™, Labcyte and IMTEK TOPSPOT™, and Bioforce™. These devices utilize various approaches to non-contact spotting, including piezo electric dispension; touchless acoustic transfer; en bloc printing from multiple microchannels; and the like. Other approaches include ink jet-based printing and microfluidic platforms. Contact printers are commercially available from TeleChem International (ARRAYIT™). Non-contact printers are of particular interest because they are more compatible with deformable hydrogel surfaces and allow for simpler control over spot size via multiple dispensing onto the same location.

Non-contact printing will typically be used for the production of arrays of dots (microdots) on the nanofibrous matrix. By utilizing a printer/spotter that does not physically contact the surface of substrate, no aberrations or deformities are introduced onto the surface, thereby preventing uneven or aberrant cellular capture at the site of the spotted material. Such printing methods find particular use with hydrogel substrates. Printing methods of interest, including those utilizing acoustic or other touchless transfer, also provide benefits of avoiding clogging of the printer aperature, e.g. where probe solutions have high viscosity, concentration and/or tackiness. Touchless transfer printing also relieves the deadspace inherent to many systems. The use of print heads with multiple ports and the capacity for flexible adjustment of spot size can be used for high-throughput, automated microarray preparation.

The total number of spots on the matrix will vary depending on the number of different conditions (e.g., material combinations) to be explored, as well as the number of control spots, calibrating spots and the like, as may be desired. Generally, the pattern present on the surface of the matrix will comprise at least 2 distinct spots, usually about 10 distinct spots, and more usually about 100 distinct spots, where the number of spots can be as high as 50,000 or higher. The spot/microdot will usually have an overall circular dimension and the diameter will range from about 10 μm to 5000 μm, or from about 100 μm and 500 μm.

Following the formation of the array of microdots of biomaterial(s), the nanofiberous cell culture matrices may be subjected to a second exposure to UV light to covalently cross link the deposited/arrayed biomaterials to the fiberous matrix. This is particularly useful for covalently linking sulfhydryl groups of proteins or peptides to the fiberous matrix. In this way, other molecules of interest, such as dyes or florescent molecules, can be covalently linked to the fiberous matrix by first attaching the molecule to a peptide linker that will cross link the molecule to the fiberous matrix following UV exposure. Additionally or alternatively, molecules may also be grafted to the fiberous matrix after being functionalized. For example, a biomolecule may be treated with oxygen or ammonia plasma to functionalize the molecule, which is then grafted to the fiberous matrix.

The methods and systems of this disclosure are useful to modulate the density of biological materials "spotted" on a cell culture substrate. For example, the maximum density of ECM molecules is dependent on several factors including: the concentration of stock solution, the solubility of ECM proteins, the porosity of the fiber matrix, and the mode of deposition (e.g., pin or piezoelectric). Controlling the amount/density of biological materials in a culture environment can modulate cell growth and differentiation. Accordingly, the spotting device can be calibrated and used to provide specific amounts of insoluble and/or soluble biological materials to select "spots" or microdots.

This disclosure provides methods and systems useful for identifying optimal conditions for controlling cellular development and maturation. For example, the methods and systems of this disclosure are useful for identifying optimal conditions that control the fate of cells (e.g., differentiating stem cells into more mature cells, maintenance of self-renewal, and the like) by controlling and optimizing the extracellular and soluble microenvironment upon which the cells are cultured in parallel array fashion for rapid high throughput techniques. A 3-dimensional cell culture microarray platform of this disclosure is useful for testing a multitude of soluble factors (e.g., growth factors, hormones, steroids and the like) and insoluble factors (e.g., extracellular matrix, cell adhesion proteins, glycoproteins and the like) individually and in combination using minimal reagents and a relatively small numbers of cells, in an automated and high throughput methodology.

With the advent of DNA robotic spotting technology, it is now possible to routinely deliver nanoliter volumes of many different materials, from interfering RNA, to peptides, to biomaterials at precise locations on a microarray substrate. ECM materials may be more difficult to manipulate due to, for example, incompatible process conditions for ECM protein spotting, extensive customization of spotting equipment, or lack of pattern fidelity (i.e. cell localization) over time. These limitations may be overcome by, for example, modifying the buffer used in a spotting device to allow for accurate ECM deposition, and the use of nanofiberous materials that permit ECM immobilization, such as hydrogel materials. The methods and systems of this disclosure are useful for spotting substantially purified or mixtures of biological proteins, nucleic acids and the like (e.g., collagen I, collagen III, collagen IV, laminin, and fibronectin) in various combinations on a standard cell culture substrate (e.g., a microscope slide) using commercially available chemicals and a conventional DNA robotic spotter. Thus, the systems and methods of this disclosure allow for a multitude of insoluble factors (e.g. extracellular matrix, biomaterials), tethered soluble factors (e.g., growth factors), or mixtures of insoluble and soluble cues to be tested in parallel on a small scale.

This disclosure provides a nanofiberous matrix comprising multiple distinct cell culture domains of arbitrary protein or polymer composition and size by using robotic spotting technology (e.g., a DNA spotting device or a similar device), to transfer nanoliter quantities of biomaterials onto a fiber matrix anchored to a solid substrate (e.g., glass, silicon, polymer or other biocompatible material used in cell culture) at desired locations.

One or more desired biological materials may be deposited as discrete "spots" on the fiberous matrix. Each spot may comprise a different biological material composition. Each spot may comprise the same biological material composition. Cells cultured on the spots may be the same or different. For example, a defined ECM material is deposited as discrete spots onto a cell culture matrix of this disclosure, and cells are then seeded within the matrix and cultured under desired culture conditions. Where the spots comprise different biological materials, the cells experience different stimuli while being cultured simultaneously but maintained in distinct spatial domains creating a cellular array.

The biomaterials or test analytes delivered to the cells in the cellular microarrays formed in the methods and systems of this disclosure may include organic and inorganic molecules, including biological molecules. For example, the analyte may be an environmental pollutant (including pesticides, insecticides, toxins, and the like); a chemical (including solvents, polymers, organic materials, and the like); therapeutic molecules (including therapeutic and abused drugs, antibiotics, and the like); biological molecules (including, e.g., hormones, cytokines, proteins, lipids, carbohydrates, cellular membrane antigens and receptors (neural, hormonal, nutrient, and cell surface receptors) or their ligands); whole cells (including prokaryotic and eukaryotic cells; viruses (including, e.g., retroviruses, herpesviruses, adenoviruses, lentiviruses); spores; and the like.

One cell type or a plurality of cell types can be used in the microarrays formed by the methods and systems of this disclosure. For example, cultures of two cell types can be performed thus allowing for co-culture of two cell types. For example, the fiberous matrix surrounding a first spot can be modified such that cells cannot attach to, or migrate to, the regions surrounding the spot. In this manner, mono-culture or co-culture involving multiple cell types and multiple ECM coatings can be tested in a single nanofiberous matrix system.

The type of biological materials (e.g., ECM materials) deposited in the microarray will be determined, in part, by the cell type or types to be cultured. For example, ECM molecules found in the hepatic microenvironment are useful in culturing hepatocytes, the use of primary cells, and a fetal liver-specific reporter ES cell line. It will be recognized that the biomaterial used in the array may be modulated by cellular interactions. For example, interaction with ECM is known to modulate matrix metalloproteinase expression, integrin activity, and matrix expression.

The effect of soluble and insoluble factors/test analytes and/or biomaterials on cells cultured in a microarray formed by the methods and systems of this disclosure can be probed or evaluated using a specific marker, or examined for cellular morphology, and the like. For example, the array can be probed for the state of differentiation using various techniques including in situ hybridization, antigenic recognition (intracellular or cell membrane), in situ PCR, or an artificial DNA-reporter construct such as GFP or beta-galactosidase. The cell array can be assessed using fluorescent microscopy, high resolution light microscopy, a confocal laser scanner (such as those commonly used for DNA microarray applications), fluorescence and absorbance plate readers, scanners, or other such equipment. In many aspects, the measurements will be made by automated microscopes, plate readers and the like. In this manner, "optimal" culture conditions, as defined by the user, can be identified for closer examination and testing using more conventional techniques.

Cells cultured in microarrays of the disclosure may be used to study cell and tissue morphology. For example, enzymatic and/or metabolic activity may be monitored in the culture by fluorescence or spectroscopic measurements on a conventional microscope. In one aspect, a fluorescent metabolite in the fluid/media is used such that cells will fluoresce under appropriate conditions (e.g., upon production of certain enzymes that act upon the metabolite, and the like). Alternatively, recombinant cells can be used in the cultures system, whereby such cells have been genetically modified to include a promoter or polypeptide that produces a therapeutic or diagnostic product under appropriate conditions (e.g., upon zonation or under a particular oxygen concentration).

Embryonic stem cells are a potential source of differentiated cells that could be used in cell therapy, drug discovery, and basic research. Current methods for differentiating embryonic stem cells in vitro are generally inefficient for generating specific lineages, and rely on the use of heterogeneous cell aggregates called embryoid bodies. Exceptions to this generalization are a few rare reports of efficient monolayer culture methods, underscoring the importance of a tightly regulated environment for efficient lineage-specific differentiation. While most studies focus on growth factors, the importance of ECM in developmental processes has increasingly been recognized. In vitro, undifferentiated mouse ES cells express integrins $\alpha 6$, $\beta 1$, $\beta 4$, $\beta 5$, laminin receptor 1, and dystroglycan; signals from ECM. Stem cell differentiation studies could therefore benefit from a parallelized culture platform of this disclosure. Monitoring can be performed using specific markers or ubiquitous cellular constituents such as actin and keratin.

This disclosure provides a cell culture matrix that can be read or analyzed by a variety of methods including, but not limited to, surface plasmon resonance, mass spectrometry, quartz crystal resonance, electron microscopy and scanning probe microscopy. In one aspect, scanning probe microscopy (SPM) such as atomic force microscopy (AFM). Use of an AFM or another type of SPM creates a methodology for a simple rapid, sensitive and high throughput method for detection of microorganisms, pathogens, biological matter, viruses, or microparticles. This method can be used to detect changes in a spot sample. Additionally, fluorescence or other methods commonly practiced for detection of biological events can be employed in the methods and systems of this disclosure.

This disclosure provides cell culture technology that can be useful for a variety of purposes, such as determining the appropriate culture conditions for differentiating stem cells into more mature cells, studying cell-matrix and growth factor interactions in a systematic manner, and potentially screening new drug molecule candidates for their effects on cells in vitro by immobilizing small volumes in degradable matrices for sustained release. Additionally, the platform can be extended for use with non-stem cells, such as primary cells (e.g. hepatocytes, fibroblasts), genetically modified cells, and transformed or cancerous cell types. A number of uses of the methods and systems will be readily apparent to one of skill in the art. For example, stem cell therapeutic companies could use such technology to optimize differentiation protocols for specific lineages. Lifescience or pharmaceutical companies could use such technology for optimizing in vitro production of recombinant proteins. Pharmaceutical companies could use a miniaturized cell culture platform to test toxicity of potential drug compounds in a parallel manner. Researchers could use such a platform to test the effects of insoluble or tethered soluble and insoluble cues on cellular differentiation.

The culture system and microarrays of the disclosure can be used in a wide variety of applications. These include, but are not limited to, screening compounds, growth/regulatory factors, pharmaceutical compounds, and the like, in vitro; elucidating the mechanisms of certain diseases, studying the mechanisms by which drugs and/or growth factors operate, diagnosing and monitoring cancer in a patient, and the production of biological products.

The methods and systems of the disclosure may be used in vitro to screen a wide variety of compounds, such as cytotoxic compounds, growth/regulatory factors, pharmaceutical agents, and the like, to identify agents that modify cell (e.g., hepatocyte) function and/or cause cytotoxicity and death or modify proliferative activity or cell function. For example, the culture system may be used to test adsorption, distribution, metabolism, excretion, and toxicology (ADMET) of various agents. The activity of a compound can be measured by its ability to damage or kill cells in culture or by its ability to modify the function of the cells. This may readily be assessed by vital staining techniques, ELISA assays, immunohistochemistry, and the like. The effect of growth/regulatory factors on the cells (e.g., hepatocytes, endothelial cells, epithelial cells, pancreatic cells, astrocytes, muscle cells, cancer cells) may be assessed by analyzing the cellular content of the culture, e.g., by total cell counts, and differential cell counts or by metabolic markers such as MTT and XTT. This may also be accomplished using standard cytological and/or histological techniques including the use of immunocytochemical techniques employing antibodies that define type-specific cellular antigens. The effect of various drugs on normal cells cultured in the culture system may be assessed. For example, drugs that affect cholesterol metabolism, e.g., by lowering cholesterol production, could be tested on a liver culture system.

The cytotoxicity to cells in culture (e.g., human hepatocytes) of pharmaceuticals, anti-neoplastic agents, carcinogens, food additives, and other substances may be tested by utilizing the cell culture microarrays of this disclosure.

This disclosure also provides a screening method comprising, generating a microarray of biomaterials on a nanofiberous cell culture matrix of this disclosure using a spotting device (e.g., a DNA spotting device) or similar device. A material spotted by the device may include soluble and/or insoluble factors that have known activity or effects on cells or may comprise factors having unknown activity of effects on cells. Cells are then contacted with the micro-spot array and a stable, growing culture is established. The cells may then be examined or alternatively, the cells are exposed to varying concentrations of a test agent. After incubation, the culture is examined to determine the effect of the material and/or test agent on a cell's morphology, growth, activity, and the like. Cytotoxicity testing can be performed using a variety of supravital dyes to assess cell viability in the liver culture system, using techniques well-known to those skilled in the art.

Similarly, the beneficial or deleterious effects of drugs or biologics may be assessed using the nanofiberous cell culture matrix of this disclosure. For example, growth factors, hormones, or drugs which are suspected of having the ability to enhance cell or tissue function, formation or activity can be tested. In this case, stable cultures are exposed to a test agent. After incubation, the cultures are examined for viability, growth, morphology, cell typing, and the like, as an indication of the efficacy of the test substance. Varying concentrations of the drug may be tested to derive a dose-response curve.

The culture systems of the disclosure may be used as model systems for the study of physiologic or pathologic conditions and to optimize the production of a specific protein.

The microarray culture system may also be used to aid in the diagnosis and treatment of malignancies and diseases. For example, a biopsy of a tissue (such as, for example, a cell biopsy) may be taken from a subject suspected of having a malignancy or other disease or disorder. The biopsy cells can then be cultured under appropriate conditions (e.g., defined factors spotted on an array) where the activity of the cultured cells can be assessed using techniques known in the art. In addition, such biopsy cultures can be used to screen agent that modify the activity in order to identify a therapeutic regimen to treat the subject. For example, the subject's tissue culture could be used in vitro to screen cytotoxic and/or pharmaceutical compounds in order to identify those that are most efficacious; i.e. those that kill the malignant or diseased cells, yet spare the normal cells. These agents could then be used to treat the subject.

Similarly, the beneficial effects of drugs may be assessed using a microarray in vitro; for example, growth factors, hormones, drugs which enhance hepatocyte formation or activity can be tested. In this case, microarray cultures may be exposed to a test agent. After incubation, the microarray cultures may be examined for viability, growth, morphology, cell typing, and the like as an indication of the efficacy of the test substance. Varying concentrations of the drug may be tested to derive a dose-response curve.

Using micropatterning of co-cultures and reagents can lead to a cell or tissue model that can be optimized for specific physiologic functions including, for example, synthetic, metabolic, or detoxification function (depending on the function of interest) in hepatic cell cultures.

The methods and systems of this disclosure may utilize co-cultures of cells in which at least two types of cells are configured in a micropattern on a substrate. Micropatterning techniques may be used to modulate the extent of heterotypic cell-cell contacts. In addition, co-cultures (both micropatterned co-cultures and non-micropatterned co-cultures) have improved stability and thereby allow chronic testing (e.g., chronic toxicity testing as required by the Food and Drug Administration for new compounds). Because micropatterned co-cultures are more stable than random cultures the use of co-cultures and more particularly micropatterned co-cultures provide a beneficial aspect to the cultures systems of the disclosure. Furthermore, because drug-drug interactions often occur over long periods of time the benefit of stable co-cultures allows for analysis of such interactions and toxicology measurements.

Typically, in practicing the methods of this disclosure, the cells are mammalian cells, although the cells may be from two different species (e.g., pigs, humans, rats, mice, and the like). The cells can be primary cells, stem cells, or they may be derived from an established cell-line. Although any cell type that adheres to a substrate can be used in the methods and systems of the disclosure (e.g., parenchymal and/or stromal cells), exemplary cell include, stem cells, epithelial cells, endothelial cells, muscle cells, neuronal cells, etc.

The methods and systems of this disclosure have been demonstrated as set forth in more detail in the following Examples. The working examples provided below are to illustrate, not limit, the disclosure. Various parameters of the scientific methods employed in these examples are described in detail below and provide guidance for practicing the disclosure in general.

EXAMPLES

Example 1—Preparation and Characterization of a Polyethylene Glycol Dimethacrylate (PEGDM) Cell Culture Matrix Fabrication of PEGDM Soft Matrices Polyethylene glycol dimethacrylate (PEGDM) with a molecular weight of 750 kDa and polyethylene oxide (PEO) (MW 400,000 kDa) were purchased from Sigma (Sigma-Aldrich, St. Louis, Mo.). An electrospinning solution composed of 3.2% wt PEGDM 750, 3.4% wt PEO, 0.4% wt of Irgacure 2959 and 93% DI $H_2O$ was mixed for 30 minutes with magnetic stir bar. PEGDM 750 photopolymerizable soft matrices were fabricated by electrospinning on a custom set up composed of a high voltage power supply, grounded collecting surface, motorized syringe pump, and a 14 mm syringe. The solution (2 ml) was spun at a distance of 26 cm from the stationary collecting surface, at a voltage of 30 kV, and a flow rate of 1.10 ml/hr. Electronspun matrices were deposited onto glass slides 25 mm×75 mm (Fischer Scientific) modified with 3-(Trimethoxysilyl)propyl methacrylate (TMPMA) (Sigma) to present methacrylate groups that bond the substrate to the glass. Substrates were subsequently introduced into an inert argon environment to remove oxygen followed by stabilization under UV exposure (352 nm light) with an average intensity of 5 $mW/cm^2$ for specific time durations.

Characterization of PEGDM Soft Matrices

FTIR Analysis:

PEGDM electrospun net samples were first loaded into a sealed liquid-cell (Sigma) in the presence of an inert argon environment to prevent oxygen contamination during IR acquisition. PEGDM double bond conversion was evaluated using a real-time mid-range fourier transform infrared spectroscopy (FTIR) (Nicolet 4700, Thermo Fisher Scientific, Waltham, Mass.) by examining the disappearance of the C=C peak within the acrylate group (~1635) on a dry specimen in the presence of UV light (15 mW/cm2) over time. To account for sample and background variation, data were normalized with the C=O peak located in the range from 1650 to 1726 $cm^{-1}$.

Scanning Electron Microscopy Imaging:

Scanning electron microscopy (FESEM, JSM-7401F, Jeol Ltd, Tokyo, Japan) was used to examine the microstructure of the electrospun PEGDM substrates in both dry and hydrated states. For hydrated samples, substrates were photopolymerized for 15 min and rinsed in DI $H_2O$ for 24 hr. To prepare for imaging, rinsed samples were shock froze in liquid nitrogen (–195 C) and lyophilized for approximately 24 hr. Image) was used to analyze changes in fiber diameter and porosity.

Fluorescent Imaging:

PEGDM soft matrices were imaged under fluorescence to observe their properties in the wet state. Rhodamine-methacrylate was introduced into the electrospun fibers and subsequently stabilized during UV exposure to provide fluorescence of the fibrous structure. PEGDM-rhodamine conjugates were then imaged using either a fluorescent microscope or a confocal laser scanning microscope.

Rheology:

Changes in storage modulus (G') of PEGDM substrates with respect to photopolymerization time were characterized using a rheometer (=5%, =1 rad/s for linear viscoelastic regime, ARES TA rheometer, TA Instruments, New Castle, Del.). PEGDM substrates, approximately 0.3 mm thickness) were deposited onto 3-(Trimethoxysilyl)propyl methacrylate modified circular coverslips (D=18 mm) and photopolymerized for 2, 5, 10, or 15 min and then rinsed in DI $H_2O$ for 24 hr. PEGDM soft matrices were tested with a parallel plate configuration. A vertical load of 5 grams was applied to all samples to prevent slippage. A strain sweep at a frequency of 1 rad/s and a frequency sweep at a strain of 5% were run on each sample. Specimens were inspected for slippage or tearing post shearing, and data collected from the linear visco-elastic region (LVE) in the strain sweep were used to determine the storage modulus G'.

ECM Protein Microarray Preparation

A printing buffer consisting of 1% glycerol and 0.2% Triton X-100 was utilized for all protein depositions. To prepare ECM arrays, stock solutions of rat collagen I (Millipore), human collagen III (Sigma), human collagen IV (Sigma), human fibronectin (Millipore), mouse laminin (Sigma), and bovine elastin (Elastin Products Company) were suspended at a concentration of 250 m/ml in printing buffer. Factorial analysis was performed to determine 64 distinct combinations from the 6 ECM proteins of interest and subsequently transferred to a predefined 384-well plate configuration. Samples were deposited on the PEGDM substrate matrix using an Aushon 2470 arrayer with 185 micron pins (Aushon BioSystems, Billerica, Mass.), to achieve a nominal diameter of 250 microns. Individual spots with 7 replicates (8 total) of each protein combination were deposited with a 500 µm pitch distance onto the PEGDM substrates. Between different sample depositions, the print needles were cleaned by sonication in cleaning solution before use. Approximately twenty ECM microarrays could be deposited simultaneously in this method within ~1 hr. Prepared ECM microarrays were stored at 4° C. in a humid environment for 24 hours before use.

Cell Culture

PEGDM soft matrix ECM microarray slides were rinsed in DI $H_2O$ for 1 hr followed by sterilization with 70% ethanol for 1hr prior to cell seeding. ECM microarray slides were equipped with 16 mm×16 mm silicon wells (Grace Bio-Labs) to partition individual microarray replicates. Rat pulmonary arterial smooth muscle cells (rPASMCs) were obtained from distal bovine vascular arteries. The cells were maintained in Dulbecco's Modified Eagle's Medium (Cellgo DMEM, Mediatech Inc, Manassas Va.), with 10% fetal bovine serum (Gemini Bio-products, West Sacramento, Calif.) and 1% Pen/Strep. Cell passages of 3-8 were used for all experiments. Bovine Aortic Smooth Muscle Cells (BASMCs) were suspended at a concentration of 10e6 cells per ml in serum free media. The cell suspension was dispensed onto the ECM microarray within the gasket region at a cell density of 10e5 cells per array and incubated for 2 hours. The arrays were then gently aspirated by submerging into a large chamber filled with prewarmed media. Culture media was changed daily.

Rat mesenchymal stem cells (rMSCs) with passages 2-5 were cultured in Dulbeccos Modified Eagles Media, with 10% defined FBS for MSCs and 1% Penn/Strep. rMSCs were suspended at a concentration of 10e6 cells per ml in serum free media. The cell suspension was dispensed onto the ECM microarray within the gasket region at a cell density of 10e5 cells per array and incubated for 4 hours. The arrays were then gently aspirated into a large chamber filled with prewarmed media. Following aspiration, culture media (10% serum) was introduced into the microarray wells. For cell cultures longer than 24 hrs the culture media was changed daily.

Immunofluorescent Staining

Cell morphology was obtained by staining for cell nuclei (DAPI) and cell cytoskeleton (phalloidin) after sample fixation in 4% formaldehyde. Fluorescently labeled cells were evaluated using an epifluorescence microscope (Zeiss, Peabody, Mass.). Cell number and morphology parameters were evaluated using Image? software.

Results 3.3.1 Nanofibrous Soft Matrix Preparation and Characterization

Nanofibrous hydrogels were prepared utilizing an electrospinning technique whereby a photopolymerizable polymer is spun onto TMSPSA functionalized glass surface, followed by UV stabilization. The presence of methacrylate groups on the glass surface allows for net stability and substrate longevity after several rinses in aqueous solution, permitting unabridged function for extended biological assays. PEGDM (MW 750) was selected for its biocompatibility, ease of manipulation, elastic qualities and commercial availability. The stabilization of PEGDM nets is achieved via a radical chain photopolymerization between the methacrylate groups in the presence of a photoinitiator and UV light (352 nm). We employed mid-range FTIR to characterize the degree of PEGDM conversion by monitoring the disappearance of the reactive acrylate peak at 1637 $cm^{-1}$ for samples over the course of 15 minutes UV exposure. Results indicated that the acrylate peak reduced by a maximum of 46% after 15 minutes of UV exposure. The lack of efficient acrylate conversion is likely due to the polymerization taking place in the dry state, reducing chain mobility and active crosslinking domains for polymerization.

We investigated the nanofibrous architecture prepared from electrospinning our PEGDM substrates using different microscopy techniques in both the wet and dry states. Copolymerizing the PEGDM nets with rhodamine-methacrylate permitted the visualization of individual fiber diameter and geometry under confocal microscopy. Employing scanning electron microscopy, we obtained high magnification images of the prepared nanofibrous substrates in both the dry and wet state. Both imaging methods indicate an approximate fiber diameter after wetting of 0.5-1 µm. Lack of beading or webbing of the electrospun nets indicates optimal spinning parameters with minimal artifacts.

To ascertain regulation of the elastic properties of the prepared nanofibrous substrates, mechanical properties were evaluated under shear using a parallel plate rheometer for PEGDM specimens prepared under different UV exposures (2, 5, 10 and 15 minutes). A positive correlation between storage modulus and UV exposure time was recorded for all specimens examined. Shear modulus increased from 400 Pa to 15 kPa after 2 and 15 minutes UV exposure respectively. The elastic properties measured are in agreement with previous work reported by Wingate et al. using a similar fabrication methodology (Wingate K, et., al., 2012. Compressive elasticity of three dimensional nanofiber matrix directs mesenchymal stem cell differentiation to vascular cells with endothelial or smooth muscle cell markers. Acta Biomater 8, 1440).

Protein Microarray Design and Optimization

Array deposition of protein microdots produced repeatable distinct microdots of average diameter 200 µm and 500 µm pitch to pitch distance. We performed several print buffer iterations using a control protein, albumin, to optimize dot presentation, homogeneity and longevity upon nanofibrous PEGDM substrates. Buffer glycerol content was found to influence the printing parameters significantly. Glycerol content positively correlated with dot circularity, whereas dot fluorescent intensity correlated negatively to elevated glycerol content. A glycerol content of 1% (v/v) was sufficient in retaining dot circularity without reducing protein intensity markedly after substrate incubation. Serial dilutions of control proteins albumin and streptavidin revealed strong protein uptake by the nanofibrous PEGDM hydrogels, with protein detected at as little as 15 µg/ml deposition concentration. A three dimensional protein microdot presentation with approximate diameter of 200 µm and substrate penetration of 50 µm was consistently achieved when printed upon PEGDM nanofibrous substrates. Optimized print conditions are amenable to global array deposition over large areas (10 mm×20 mm) with minimal perturbations of array organization and layout.

We further assessed printing efficiency using several extracellular matrix (ECM) proteins. Visual confirmation of collagen I microdots was detectable at similar concentrations to the control proteins (15-250 µg/ml). We designed and printed a combinatorial ECM microarray comprised of 6 ECM proteins, resulting in 64 total conditions (rows) in replicates of eight (columns). We confirmed protein retention for all ECM proteins through antigenic immunostaining with collagen I and collagen IV immunofluorescence. For all proteins investigated, immunofluorescence associated well with expected distribution and intensity. Distinct immunofluorescent detection of specific ECM proteins indicates successful deposition of combinatorial designs.

Rat Mesenchymal Stem Cell Adhesion within 3D ECM Microarrays

Figure 1B:
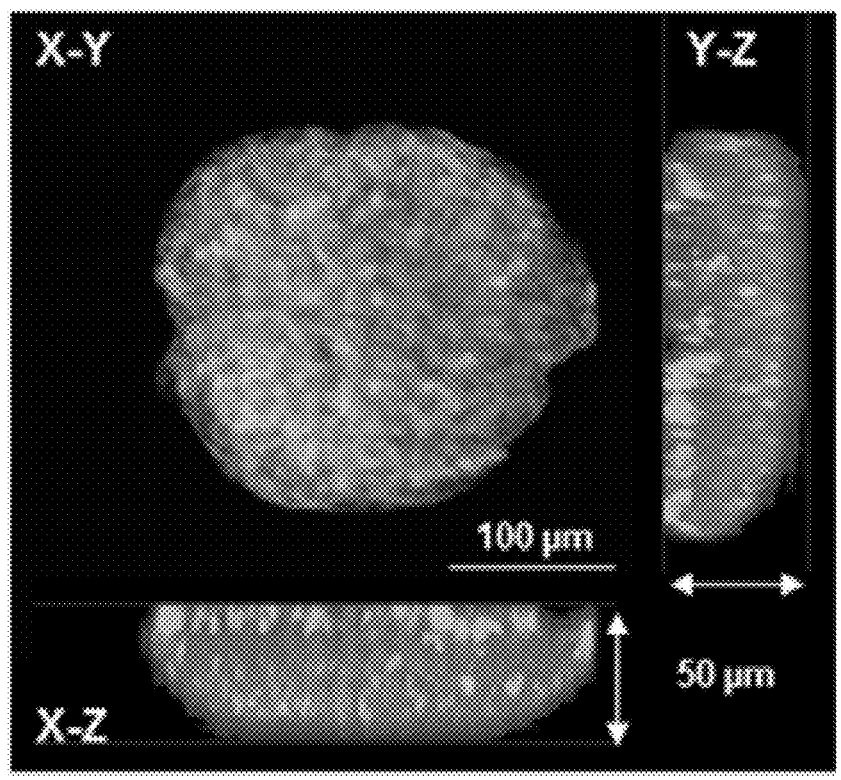
" FIG. 1B shows the three-dimensional rendering of a rMSC cellular dot formed on a cellular matrix of this disclsoure.

Subsequent to the combinatorial ECM microarray design and optimization, we proceeded to validate the biocompatibility and selective attachment of stem cells on the ECM microarray substrates. We seeded rat mesenchymal stem cells of late passage (p11) to verify the selective attachment of cells to distinct protein dots. We chose a late passage stem line for the preliminary adhesion study as we found this provided improved adhesion to the protein microdots, likely a result of a further differentiated stem line. The rMSCs attached preferentially to the microarrayed regions with little to no attachment observed on the pure PEGDM nanofibrous substrate (FIG. 1A). Furthermore, upon closer inspection, several of the distinct cellular islands represented three dimensional neo-tissue microdomains of thickness approximately 50 µm (FIG. 1B). Staining for cell nuclei identified distinct cell populations associated with the ECM protein depositions. This attachment of rMSCs to the ECM microarrays demonstrates the ability of stem cells to selectively adhere to the microarrayed regions without dot to dot communication.

Figure 2:
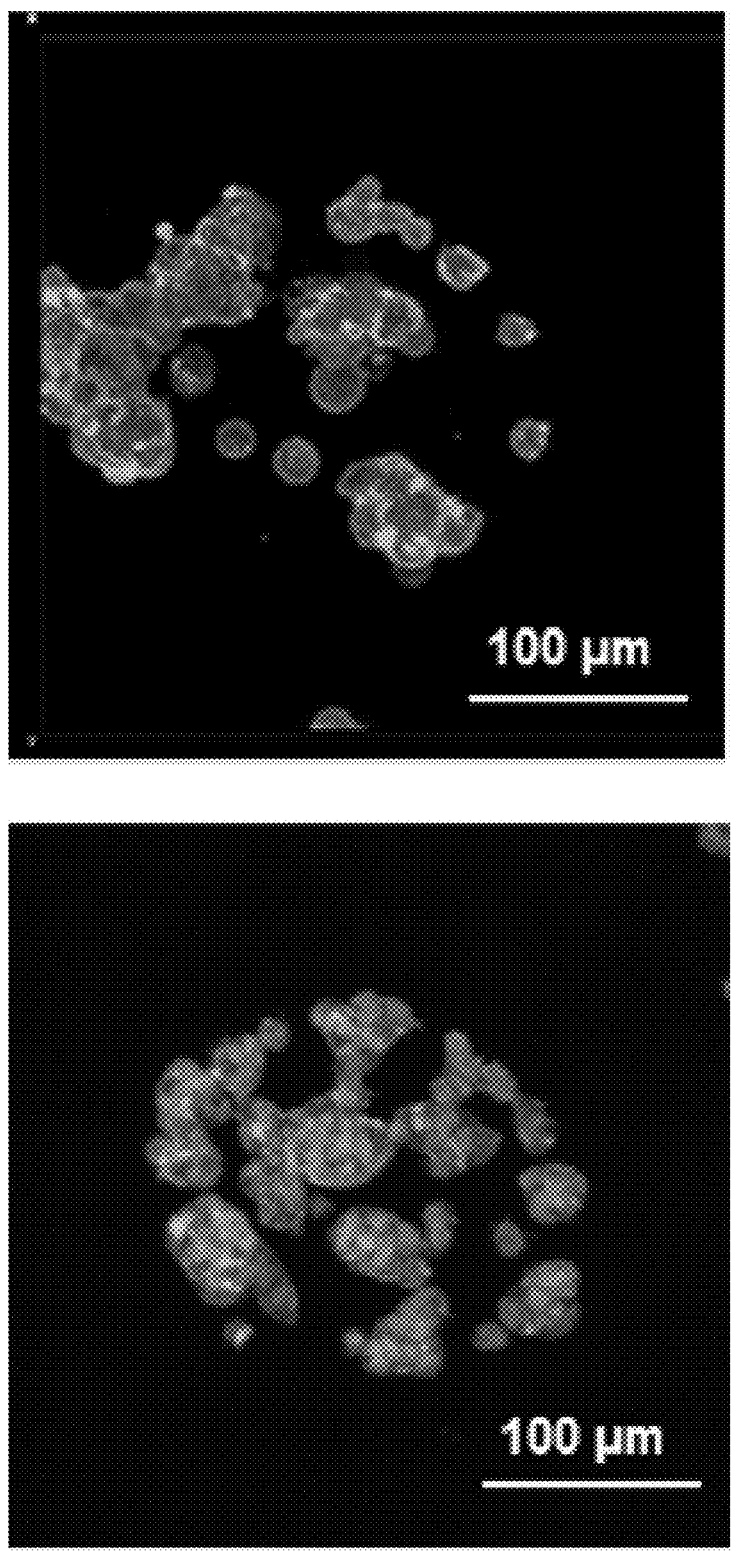
FIG. 2 shows the selective adhesion of rMSCs on ECM microarrays with different elasticity, 15 min. UV exposure (top photo) and 5 min. UV exposure (bottom photo).

To uncover the effects of substrate elasticity and ECM combination on cellular adhesion, we evaluated the 24 hr. culture of rMSCs on ECM microarrays prepared under two UV exposures, 5 and 15 minutes respectively. FIG. 2 depicts the unique adhesion of rMSCs on stiff (15 min. UV)(top photo) and soft (5 min. UV)(bottom photo) nanofibrous substrates. Cellular attachment and spreading was confirmed for both elasticities, with improved spreading detected for the softest condition (bottom photo).

To ascertain the effects of ECM composition on rMSC attachment, cellular microarrays were stained for cell nuclei and analyzed at 24 hrs. Each protein combination had detectable levels of fluorescence with pure elastin representing the least favorable adhesion point, and the elastin: fibronectin:collagen IV the most favorable point for adhesion of rMSCs. Generally, protein dots consisting of collagen IV or combined with other collagens (I and III) lead to improved cellular attachment. Likewise, combinations comprised mainly of laminin or elastin proved to have the least adhesive strength.

Effect of ECM Composition on rMSCs Behavior and Fate Commitment

To explore the potential to modulate stem cell differentiation events, we cultured rMSCs within our ECM microarrays for 24 to 72 hours and subsequently monitored for the early vascular marker PECAM. At 72-hour cell culture, rMSCs are found to spread significantly within the ECM microdots, which, at 24 hours, were found to still be significantly round. The expression of the early vascular marker was detectable at significant intensities after 72-hour cell culture. Differentiation capacity was found to be significantly affected by underlying protein combination presented. The greatest expression was found with protein dots comprised of fibronectin combined with the collagens (I, III, IV), while the least was generally found with combinations of elastin or laminin.

These data demonstrate that we developed a high throughput method that allows for the rapid screening of a diversity of engineered microenvironments with tunable matrix elasticity and geometry, combined with specific ECM protein combination and/or concentration.

Example 2—Preparation and Characterization of a Photoclickable Thiol-Ene Poly(Ethylene Glycol) Hydrogel Cell Culture Matrix We developed a microarray platform based on electrospun nanofibrous photoclickable thiol-ene poly(ethylene glycol) hydrogels. Thiol-ene polymerizations proceed by an orthogonal, step-growth mechanism where one thiol reacts with one ene leading to a highly homogenous distribution in crosslinks, thus imparting a good control over substrate elasticity. Furthermore, it allows for the subsequent modification of the already prepared electrospun hydrogel substrates with ECM molecules such as peptides with high reactivity and specificity.

Figure 3A:
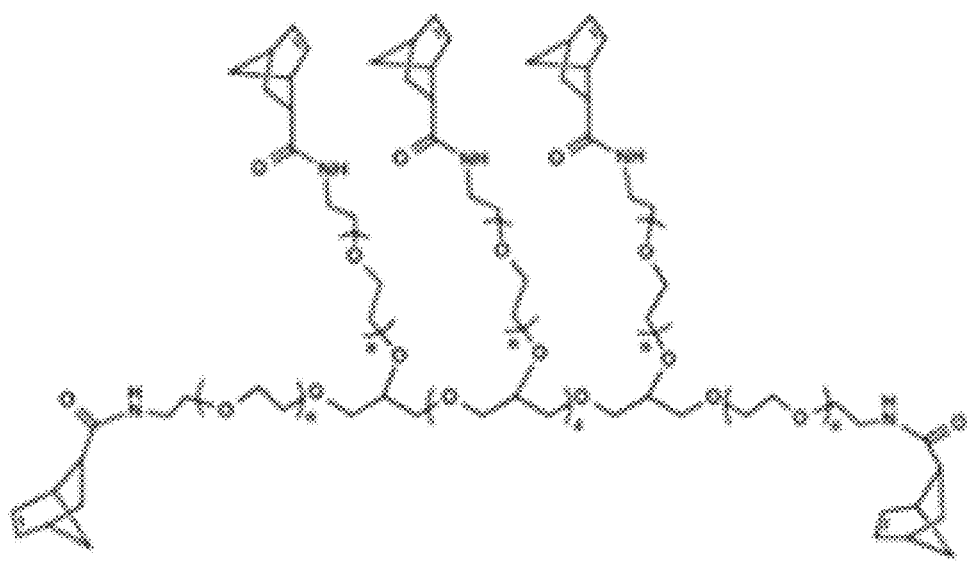
FIG. 3A shows the chemical structure of 4-arm PEG-5K-norbornene (PEGNB).
Figure 3B:
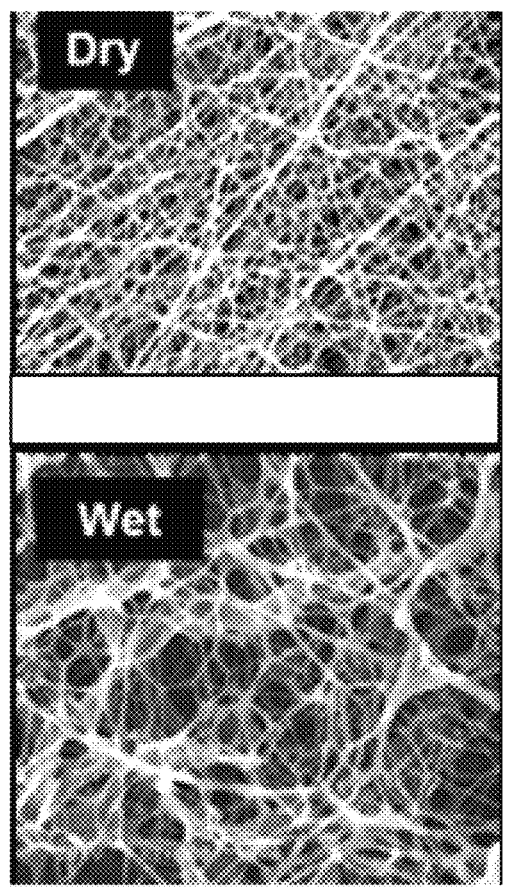
FIG. 3B shows a scanning electron microscope (SEM) image of dry and hydrated thiol-ene poly(ethylene glycol) electrospun hydrogels of this disclosure.

Preparation and Characterization of Electrospun Thiol-Ene Hydrogel Platform:

Four-arm Poly(ethylene glycol) norbornene (PEGNB; MW: 5 kDa) was prepared as described elsewhere (Roberts J. J., Bryant S. J., Biomaterials 2013, 34(38), 9969-79). PEGNB (5-10 wt %, FIG. 3A), polyethylene dithiol (1 kDa; thiol:ene=0.9), poly(ethylene oxide) (3-7 wt %; MW: 400 kDa), and Irgacure 2959 (0.1 wt %) were dissolved in DI water. Electrospun hydrogels were prepared by using a custom set up using a 14-mm syringe at 30 kV. Needle-to-collector distance (20-26 cm) and flow rate (0.4-1.2 ml/hr) were varied as desired. Electrospun fibers were collected on a glass slide (25 mm×75 mm) previously modified with 3-(mercaptopropyl) triethoxysilane. Substrates were subsequently exposed to UV (352 nm light) with an average intensity of 5 mW/cm2 for specific time points. Scanning electron microscopy was used to examine the microstructure of the electrospun hydrogel substrates in both dry and hydrated states. For hydrating, samples were soaked in deionized water for 1 or 24 hours. Hydrated samples were shock frozen in liquid nitrogen and lyophilized for 48 hours for SEM imaging (FIG. 3B). Image J was used to measure fiber diameter. Elastic properties of the electrospun hydrogels were characterized using parallel plate rheometry.

Microarray Printing

Microarrays were prepared using a 2470 Aushon arrayer. A printing buffer consisting of 1% glycerol and 0.2% Triton X-100 was utilized for ALEXA FLUOR™ 488 or 546-05 maleimide printing. Prepared microarrays were stored at 4° C. in a humid environment for 24 hours before confocal imaging.

Results

In this study, we developed electrospun hydrogel platform using thiol-ene chemistry. The diameter of the electrospun nanofibers ranged from 200-600 nm in the dry state. There was a 2 to 4-fold increase in fiber diameter when substrates were soaked and imaged after lyophilization. The elastic modulus of the substrates ranged from 1-5 kPa. Extracellular matrix (ECM) protein molecules were deposited by combinatorial printing on these electrospun hydrogel substrates. As a proof of concept, we have demonstrated that maleimide dyes can be selectively printed with high specificity. These studies indicate that this electrospun hydrogel platform is highly tunable and we can create substrates with different elastic properties by varying the molecular weight, weight %, and thiol:ene ratio. Substrates with higher elastic modulus (to cover the entire range of elasticity) can be prepared, and ECM molecules relevant for stem cell differentiation can be printed on these substrates. These data demonstrated that we have developed a highly tunable platform with 3-D nanofibrous hydrogels to facilitate high-throughput combinatorial screening of engineered microenvironments for optimizing stem cell differentiation.

What is claimed is:

1. A method of high throughput combinatorial screening of engineered microenvironments comprising:
   a. forming an in vitro cell culture matrix comprising:
      i. a hydrogel fiber anchored to a solid support;
      ii. biomaterial microdots arrayed on the hydrogel fiber; and,
      iii. at least one mammalian cell seeded within the hydrogel fiber,
   b. staining by immunofluorescence a protein in the at least one mammalian cell and
   c. quantifying observed immunofluorescence from the immunofluorescence staining of the protein by microscopy and computer aided image acquisition, wherein the quantified immunofluorescence is a measure of at least one activity of the at least one mammalian cell selected from the group consisting of gene expression, cell function, metabolic activity, and cellular morphology.

2. The method of claim 1, wherein the forming of the in vitro cell culture matrix comprises forming the hydrogel fiber by a fabrication technique selected from electrospinning, electrospraying, spin-coating, and deposition by dipping.

3. The method of claim 1, wherein the biomaterial is at least one compound selected from a polysaccharide, a proteoglycan, a glycosaminoglycan, a cell membrane bound protein, a peptide signaling motif, a hormone, collagen I, collagen type II, collagen III, collagen IV, fibronectin, laminin, chitosan, elastin, entactin, fibronectin, tenascin, heparin sulfate, chondroitan sulfate, dermaten sulfate, and karatan sulfate.

4. The method of claim 1, wherein the at least one mammalian cell is a stem cell.

5. The method of claim 1, further comprising contacting the at least one mammalian cell with a test agent prior to measuring the at least one activity of the at least one mammalian cell.

6. The method of claim 5, wherein the test agent is at least one of a growth factor, a hormone, a putative anti-cancer compound, a cell-surface protein inhibitor, a putative angiogenesis inhibitor, or a modulator of Epithelial-Mesenchymal Transition (EMT).

* * * * *